US005753222A

United States Patent [19]
Marrone et al.

[11] Patent Number: 5,753,222
[45] Date of Patent: May 19, 1998

[54] ANTIBIOTIC-PRODUCING STRAIN OF BACILLUS AND METHODS FOR CONTROLLING PLANT DISEASES

[75] Inventors: Pamela Gail Marrone; Sherry D. Heins; Denise C. Manker, all of Davis; Desmond R. Jiménez, Woodland, all of Calif.; Richard K. Bestwick, Portland, Oreg.; George J. Vandemark, Irapuato, Mexico

[73] Assignee: Agritope, Inc., Beaverton, Oreg.

[21] Appl. No.: 746,893

[22] Filed: Nov. 18, 1996

[51] Int. Cl.$^6$ .............................. A01N 63/00; C12N 1/00
[52] U.S. Cl. .................................. 424/93.462; 424/93.46; 424/123; 424/404; 424/405; 424/115; 435/71.1; 435/71.2; 435/71.3; 435/252.31; 435/839
[58] Field of Search .............................. 435/71.1, 71.2, 435/71.3, 252.31, 839; 424/93.46, 115, 93.462, 123, 404, 405

[56] References Cited

U.S. PATENT DOCUMENTS

| | | |
|---|---|---|
| 4,582,704 | 4/1986 | Baker. |
| 5,047,239 | 9/1991 | Pusey. |
| 5,049,379 | 9/1991 | Handelsman et al.. |
| 5,061,495 | 10/1991 | Rossall. |

FOREIGN PATENT DOCUMENTS

| | | |
|---|---|---|
| WO 94/09630 | 5/1994 | WIPO. |

OTHER PUBLICATIONS

Schwinn et al., "Control with chemicals" Advances in Plant Pathology: vol. 7: *Phytophtohora infestans,* the Cause of Late Blight of Potato, Ingram et al., eds., Academic Press, San Diego, (1991) 8:225–266.
Stabb et al., "Zwittermicin A –producing strains of *Bacillus cereus* from diverse soils" *Appl. Environ. Microbiol.* (1994) 60:4404–4412.
Milner et al., "Production of Kanosamine by *Bacillus cereus* UW85" *Appl. Environ. Microbiol.* (1996) 62:3061–3065.
He et al., "Zwittermicin A, an antifungal and plant protection agent from *Bacillus cereus*" *Tetra. Lett.* (1994) 35:2499–2502.
Osburn et al. "Effect of *Bacillus cereus* UW85 on the yield of soybean at two field sites in Wisconsin" *Am. Phytophataol. Soc.* (1995) 79:551–556.
Smith et al., "Suppression of cottony leak of cucumber with *Bacillus Cereus* strain UW85" *Plant Disease* (1993) 77:139–142.
Leifert et al., "Antibiotic production and biocontrol activity by *Bacillus subtilis* CL27 and *Bacillus pumilus* CL45" *J. Appl. Bacteriol.* (1995) 78–97–108.
Sholberg et al., "Biocontrol of postharvest diseases of apple using Bacillus spp. isolated from stored apples" *Can. J. Microbiol.* (1995) 41:247–252.
Swinburne et al., "Production of antibiotics by *Bacillus subtilis* and their effect on fungal colonists of apple leaf scars" *Trans. Br. mycol. Soc.* (1975) 65:211–217.
Singh et al., "*Bacillus subtilis*as a control agent against fungal pathogens of citrus fruit" *Trans. Br. mycol. Soc.* (1984) 83:487–490.

Ferreira et al., "Biological control of *Eutypa lata* on grapevine by an antagonistic strain of *Bacillus subtilis*" *Phytopathol.* (1991) 81:283–287.
Baker et al., "Inhibitory effect of *Bacillus subtilis* on *Uromyces phaseoli* and on developement of rust pustules on bean leaves" *Phytopathol.* (1983) 73:1148–1152.
Pusey et al., "Pilot tests for commerical production and application for *Bacillus subtilis* (B–3) for postharvest control of peach brown rot" *Plant Disease* (1988) 72:622–626.
McKeen et al., "Production and partial characterization of antifungal substances antagonistic to *Monilinia fructicola* from Bacilus subtilis" *Phytopathol.* (1986) 76:136–139.
Asante et al., "Characterization of fungistatic substances produced by a bacillus antagonistic to ceratocystis ulmi" *Phytopathol.* (1964) 54:819–822.
Babad et al., "An antifungal polypeptide produced by *Bacillus subtilis* " *Nature* (1952) 170:618–619.
Burachik et al., "Three antifungal polypeptides from *Bacillus subtilis* " *Experientia* (1964) 20:504–505.
Johnson et al., "Eumycin–a new antibiotic active against pathogenic fungi and higher bacteria, including bacilli of tuberculosis and diptheria" *J. Bacteriol.* (1946) 51:591.
Landy et al., "Bacillomycin: An antibiotic from *Bacillus subtilis* active against pathogenic fungi" *Proc. Soc. Exp. Bio. Med.* (1948) 67:539–541.
Michener et al., "Two antifungal substances from *Bacillus subtilis* cultures" *Arch. Biochem.* (1959) 22:208–214.
Campbell, *Biological Control of Microbial Plant Pathogens.* Cambridge University Press. A title page and table of contents are included herewith.
Handelsman et al., "Biological control of damping–off of alfalfa seedlings with *Bacillus cereus* UW 85" *Appl. Environ. Microbiol.* (1990) 56:713–718.
*Westcott's Plant Disease Handbook,* 4th ed., Revised by R. Kenneth Horst, PhD., (1979) pp. 110–113; 138–143.
Rodgers, "Potential of biopesticides in agriculture" *Pestic Sci.* (1993) 39:117–129.
Silo–Suh et al., "Biologicl activities of two fungistatic antibiotics produced by *Bacillus cereus* UW85" *Appl. Environ. Microbiol.* (1994) 60:2023–2030.

*Primary Examiner*—Herbert J. Lilling
*Attorney, Agent, or Firm*—Morrison & Foerster LLP

[57] ABSTRACT

The present invention relates to a novel strain antibiotic-producing *Bacillus subtilis* which is effective against plant fungal and bacterial infections. The invention also includes methods of protecting plants from fungal and bacterial infections comprising the step of applying to the plant an effective amount of the antibiotic-producing *Bacillus subtilis,* the antibiotic produced by the antibiotic-producing *Bacillus subtilis* or a combination thereof, optionally further comprising another antibiotic-producing bacterial strain and/or a chemical pesticide. The invention includes methods of treating fungal and bacterial infections using whole broth cultures or supernatants obtained from cultures of antibiotic-producing *Bacillus subtilis* cultures. The invention also includes treating plant infections using a combination of whole broth and/or supernatant obtained from the antibiotic-producing strain of *Bacillus subtilis* optionally in combination with chemical pesticides. Also provided is the novel bacterial strain and the antibiotic produced by the novel strain.

9 Claims, No Drawings

ANTIBIOTIC-PRODUCING STRAIN OF BACILLUS AND METHODS FOR CONTROLLING PLANT DISEASES

TECHNICAL FIELD OF THE INVENTION

The present invention is in the field of biopesticides. More particularly, this invention describes the use of a bacterial strain to control fungal and bacterial plant diseases. This invention also relates to novel fungicidal and bactericidal antibiotic compounds produced by the bacterial strain. The invention further relates to fungicidal and bactericidal compositions comprising these compounds either alone, or in combination with other pesticides and the use of these compositions either alone, or in fermentation broths in combination with the antibiotic-producing bacterial strain to control plant diseases.

BACKGROUND OF THE INVENTION

Various microorganisms that produce antibiotics useful for controlling plant diseases are well known in the art. Although a number of biological pesticides have been identified for the control of various plant diseases of agronomic and horticultural importance, most pesticides currently in use are synthetic compounds. Many of these synthetic compounds are chemical fungicides, are classified as carcinogens by the EPA and are toxic to wildlife and other non-target species. Moreover, pathogens may develop resistance to chemical pesticides. (See, e.g., Schwinn et al., p. 244, ADVANCES IN PLANT PATHOLOGY: *PHYTOPH-THORA INFESTANS*, THE CAUSE OF LATE BLIGHT OF POTATO (Academic Press, San Diego 1991)).

Biological control and natural products offer an attractive alternative to synthetic chemical fungicides. Moreover, biopesticides (living organisms and the compounds naturally produced by these organisms) can be safer, more biodegradable, and less expensive to develop than synthetic chemical fungicides.

Screening programs have identified certain *Bacillus sp.* (*B. sp.* includes *B. subtilis, B. cereus, B. mycoides, B. anthracis* and *B. thuringiensis*) strains that exhibit antifungal activity. (See, e.g., Stabb et al. (1990) *Applied Environ. Microbiol.* 60(12):4404–4412). These strains have been shown to produce zwittermicin-A and/or "antibiotic B," now known as kanosamine (Milner et al. (1996) *Appl. Environ. Microbiol* 62:3061–3065), two antibiotic agents that are effective against the soil borne disease "damping-off" caused by *Phytophthora medicaginis, Phytophthora nicotianae, Phytophthora aphanidermatum* or *Sclerotinia minor.* (See, Stabb et al., supra). Zwittermicin A is a water-soluble, acid-stable linear aminopolyol molecule. (See, He et al. (1994) *Tetra. Lett.* 35(16):2499–2502). U.S. Pat. No. 5,049,379 to Handelsman et al. describes how zwittermicin A-producing *B. cereus* can be used to control the below-ground seedling diseases "root rot" and "damping off" in alfalfa and soybean. When the seed is coated with zwittermicin-A produced by *B. cereus* ATCC 53522, the pathogenic activity of the root rot fungus is inhibited. Similarly, application of spore-based formulations of certain *B. cereus* strains to soybean seeds or the soil surrounding the seeds has been shown to improve soybean yield at field sites. (See, Osburn et al. (1995) *Am. Phytophathol. Soc.* 79(6): 551–556). Methods of applying biopesticides are well known in the art and include, for example, wettable powders, dry flowables, microencapsulation of effective agents, liquid or solid formulations and antibiotic fractions obtained from suitable cultures. (See, e.g., U.S. Pat. No. 5,061,495 to Rossall or U.S. Pat. No. 5,049,379 to Handlesman).

Smith et al. (1993) *Plant Disease* 77(2):139–142 report that the activity of the soil-borne fungus, *Pythium aphanidermatum,* that causes cottony cucumber leak can be suppressed using zwittermicin-producing *B. cereus* strain UW85. Liefert et al. (1995) *J Appl. Bacteriol* 78:97–108 report the production of anti-Botrytis and anti-*Alternaria brassicicola* antibiotics by two Bacillus strains, *B. subtilis* CL27 and *B. pumilis* CL45. The whole broth and cell-free filtrates were active against Botrytis and Alternaria in in vitro tests and were active against Botrytis in in vivo small plant tests on Astilbe. The authors identified three antibiotics produced by the *B. subtilis* strain CL27, two of which were thought to be peptides and one non-peptide. Unlike the bacterial strains of the present invention, the antibiotics produced by the *B. pumilis* strain CL45 demonstrated only in vitro activity, no in vivo activity was demonstrated. In addition, unlike the bacterial strains of the present invention, neither strain produced the antibiotics when cultured in potato dextrose broth.

A lipoprotein antibiotic having a molecular weight of approximately 63,500 daltons that demonstrates activity against gram-positive bacteria but not gram-negative bacteria is disclosed in U.S. Pat. No. 5,061,495. In addition, this antibiotic is active against wheat powdery mildew caused by *Erysiphe graminis* and gray mold caused by Botrytis fabae. Unlike the antibiotics of the present invention, this antibiotic is insoluble in water at a pH of 5.0 or below.

Other research on the use of *Bacillus sp.* and *Bacillus subtilis* as biocontrol agents of fungal plant pathogens has been reported but the research does not characterize the antifungal and antibacterial antibiotics produced by the Bacillus. (See, e.g., Sholberg et al. (1995) *Can. J Microbial* 41:247–252; Swinburne et al. (1975) *Trans. Brit. Mycol Soc.* 65:211–217; Singh and Deverall (1984) *Trans. Brit. Mycol Soc.* 83:487–490; and Ferreira et al. (1991) *Phytopathol.* 81:283–287). Baker et al, (1983) *Phytopathol.* 73:1148–1152, reported an antifungal *Bacillus subtilis* antibiotic as having a molecular weight of >100,000 daltons, but then a subsequent report by Baker and Stavely (1983) U.S. Pat. No. 4,582,704, reports the *B. subtilis* antibiotic as having a molecular weight of 5–10,000 daltons. Pusey et al. (1988) *Plant Dis.* 72:622–626, Pusey and Robins, U.S. Pat. No. 5,047,239, and McKeen et al. (1986) *Phytopathol.* 76:136–139 have reported on the control of post-harvest fruit rot using *B. subtilis.* McKeen et al., supra, have shown that antibiotics similar to the low molecular weight iturin cyclic polypeptides contribute to the fungicidal activity of *B. subtilis.* Cyclic polypeptides such as mycosubtilin, eumycin, bacillomycin and the iturin series have been reported to inhibit several plant pathogenic and other fungi. (Asante and Neal (1964) *Phytopathol.* 54:819–822; Babad et al. (1952) *Nature* 170:618–619; Burachik et al. (1964) *Experientia* 20:504–505; Johnson and Burdon (1946) *J Bacteriol.* 51:591; Landy et al. (1948) *Proc. Soc. Exp. Biol. Med.*67:539–541; and Michener and Snell (1959) *Arch. Biochem.* 22:208–214). This series of related compounds has a molecular weight ranging from 1029 to 1183 kD, unlike the antibiotic produced by the *Bacillus subtilis* of the present invention.

DISCLOSURE OF THE INVENTION

A novel antibiotic with antifingal and antibacterial activity isolated from a novel *Bacillus subtilis* is provided. A method of treating or protecting plants from fungal and bacterial infections comprising the step of applying an effective amount of an antibiotic-producing *Bacillus subtilis,* the novel antibiotic or a combination thereof is provided. In addition, at least one other antibiotic-producing microorganism can be combined with the antibiotic-producing bacterial strain and/or novel antibiotic of the present invention. The antibiotic-producing *Bacillus subtilis* can be provided as a suspension in a whole broth culture. Also provided are methods of treating or protecting plants by applying an antibiotic-containing supernatant obtained from a whole broth culture of the novel antibiotic-producing *Bacillus subtilis*.

MODES OF CARRYING OUT THE INVENTIONS

The present invention results from the finding that a novel antibiotic produced by a novel antibiotic-producing bacterial strain is effective at treating and protecting plants from fungal and bacterial infections. Thus, the invention includes methods of preventing and treating fungal and bacterial diseases in plants using the novel antibiotic-producing bacterial strain or novel antibiotic-containing supernatants obtained from the bacterial strain or the novel isolated, purified antibiotic obtained from the novel bacterial strain.

In one aspect, the invention comprises applying the novel antibiotic and/or the novel antibiotic-producing bacterial strain to a plant in sufficient amounts to prevent or treat fungal and bacterial infections. The bacterial strain can be provided as a suspension in a whole broth culture. In another aspect, the invention encompasses preventing or treating fungal and bacterial infections by applying an effective amount of the novel antibiotic in a supernatant obtained from the novel antibiotic-producing bacterial strain. In yet another aspect, the invention encompasses the novel bacterial strain and the novel antibiotic produced thereby. Further aspects of the invention are described below.

DEFINITIONS

As used herein, "biological control" is defined as control of a pathogenic organism by the use of a second organism. Known mechanisms of biological control include enteric bacteria which control root rot by out-competing fungi for space on the surface of the root. Bacterial toxins, such as antibiotics, have been used to control pathogens. The toxin can be isolated and applied directly to the plant or the bacterial species may be administered so it produces the toxin in situ.

The term "fungus" or "fungi" includes a wide variety of nucleated, sporebearing organisms which are devoid of chlorophyll. Examples of fungi include yeasts, mildews, molds, rusts, and mushrooms.

The term "bacteria" includes any prokaryotic organism that does not have a distinct nucleus.

"Fungicidal" means the ability of a substance to increase mortality or inhibit the growth rate of fungi.

"Antibiotic" includes any substance which is able to inhibit or kill a microorganism. Antibiotics may be produced by another microorganism or by a synthetic or semisynthetic process. The term, therefore, includes substances which inhibit or kill fungi, such as, zwittermicin-A, kanosamine and the like. The novel antibiotic of the present invention inhibits both bacteria and fungi.

The term "culturing" refers to the propagation of organisms on or in media of various kinds. "Whole broth culture" refers to a liquid culture containing both cells and media. "Supernatant" refers to the liquid broth remaining when cells grown in broth are removed by centrifugation, filtration, sedimentation or other means well known in the art.

An "effective amount" is an amount sufficient to effect beneficial or desired results. An effective amount can be administered in one or more administrations. In terms of treatment and protection, an "effective amount" is that amount sufficient to palliate, ameliorate, stabilize, reverse, slow or delay the progression of fungal or bacterial disease states.

Unlike known treatments for plant diseases, the method of this invention employs a biocontrol agent, AQ153, to control fungal and bacterial infections. Thus, in one aspect, the present invention entails a method of treating or protecting a plant from fungal and bacterial infections comprising the step of applying an effective amount of the antibiotic-producing bacterial strain AQ153 to the plant.

The bacterial strain of this invention may be grown in any conventional growth medium that supports *Bacillus sp*. Examples of suitable broth for culturing *Bacillus sp*. include, but are not limited to potato dextrose broth, a broth composed of peptone, dextrose, yeast extract, malt extract, proflo cottonseed extract and soy flour and a broth made of half-strength trypticase soy broth. Solid substrates are also suitable for growing *Bacillus sp*. Growth procedures may also be readily scaled up to large fermentors by methods well known in the art.

In one embodiment, the antibiotic-producing bacterial strain is applied as a suspension in a whole broth culture. In preferred embodiments, the bacterial suspension provides protection from or treatment of fungal or bacterial infections caused by organisms including, but not limited to, *P. infestans* (late blight), *B. cinerea* (gray-mold), *P. syringae* (bacterial speck), *Plasmopara viticola* (grape downy mildew), *Puccinia reconditor* (rust), *Rhizoctonia solani, Alternaria solani, Erwinia herbicola, Monilia fructicola,* and *Pythium ultimum*.

The bacterial strain of the present invention, AQ153, which was deposited with the American Type Culture Collection on Sep. 21, 1994 under the provisions of the Budapest Treaty on the International Recognition of the Deposit of Microorganisms for the Purpose of Patent Procedure under Accession No. ATCC 55614 does not produce zwittermicin A but it does produce another water-soluble antibiotic. However, unlike previously-described, water-soluble antibiotics produced by Bacillus, this antibiotic does not precipitate at pH 5 and is active against gram-negative bacteria. Moreover, AQ153 produces this antibiotic when grown in potato dextrose broth (PDB).

Thus, the invention also encompasses an antibiotic compound for protecting and treating plants from fungal and bacterial infections comprising an antibiotic obtained from AQ153 that is water soluble, has a molecular weight greater than 10,000 daltons, is stable to at least 70° C., is produced when the novel bacterial strain AQ153 is cultured in potato dextrose broth and is soluble at a pH ranging from 3.0 to 11.0. The invention also encompasses methods of protecting and treating plants from fungal and bacterial infections comprising applying the bacterially-produced, water-soluble antibiotic having a molecular weight greater than 10,000 daltons, that is stable up to 70° C., and is soluble at a pH ranging from 3.0 to 11.0, to plants in need of such protection or treatment.

In another aspect, the present invention provides a method of protecting and treating plants from fungal and bacterial infections comprising applying an effective amount of a supernatant obtained from a whole broth culture of the antibiotic-producing bacterial strain AQ153 within the present invention. The supernatant may be obtained by means well known in the art including centrifugation, filtration, sedimentation or the like. The supernatant may be used immediately, refrigerated or frozen for future use. The supernatant may be diluted, for example, to 25% full strength, preferably it is used at greater than 50% full strength, more preferably at greater than 75% full strength and even more preferably at full strength.

In order to achieve good dispersion and adhesion of the whole broth cultures and antibiotic-containing supernatants within the present invention, it may be advantageous to formulate the whole broth cultures and the supernatants with components that aid dispersion and adhesion. Suitable formulations will be known to those skilled in the art The antibiotic-containing supernatants and whole broth cultures and compositions comprising at least one antibiotic and at least one culture of the antibiotic-producing bacterial strain AQ153 can be formulated as wettable powders, soluble powders in wettable granules, dry flowables, aqueous flowables, wettable dispersible granules, emulsifiable concentrates, aqueous suspensions, and the like, or can be microencapsulated in a suitable medium, and the like. Suitable formulations will be known to those skilled in the art.

All patents and publications cited herein are incorporated by reference.

The following examples are provided to illustrate the invention. These examples are not to be construed as limiting.

EXAMPLES

Example 1

Characterization of Strain AQ153
AQ153 Produces a Water-Soluble Antibiotic

AQ153 is a strain of *Bacillus subtilis* that produces a novel compound having antibiotic properties. To determine the nature of the novel antibiotic produced by this strain, the following experiments were performed. AQ153 was grown in 50 mL of potato dextrose broth (PDB) for 3 days. The culture was then extracted with 50 mL of ethyl acetate and centrifuged to separate the layers. The aqueous extract was dried completely and resuspended a sterile deionized water. At pH 3.0 to 11.0, no precipitation was visible. A 250 μL aliquot of potato dextrose agar (PDA) was placed in each well of a 96-well microtiter plate. Test samples of the AQ153 antibiotic were prepared by making serial dilutions of the ethyl acetate extract. 20 μL of each dilution of the resuspended aqueous extract was added to separate wells. A 20 μL aliquot of a *Botrytis cinerea* spore suspension was then added to each well. After 6 days, the amount of *B. cinerea* growth was recorded. *B. cinerea* grew in all control wells and in all ethyl acetate extract wells. Growth was completely inhibited only in the wells containing aqueous extract.
AQ153 Does Not Produce Zwittermicin-A Bacterial strains known to produce zwittermicin-A exhibit synergistic effects with *Bacillus thuringiensis*. (See, Manker et al., WO/9409630). Therefore, to determine whether AQ153 produces zwittermici-A, cultures of slected strains were mixed with Javelin® (*B. thuringiensis*) and observed for synergistic activity. More specifically, 50 mL cultures of AQ153 and known zwittermicin-producing strains AQ175 (ATCC No. 55608) and AQ177 (ATCC No. 55609) were grown in tryptic soy broth (TSB, Difco, Detroit, Mich.) for three days at 29° C. The whole broth cultures were centrifuged at 4,000 rpm for 20 minutes. The supernatants were decanted and stored at −20° C. One milliliter of each supernatant was used as a stock while 1 mL was diluted with 500 μL of sterile distilled water. Eight serial dilutions were then made from the diluted sample.

Javelin® WG (0.0521 g) was mixed with 50 mL of distilled water to produce a 1000 μL stock solution. The stock solution was then serially diluted in distilled water to give eight 0.5 mL solutions. A 50:50 mixture of the Javelin® stock solution and each supernatant stock solutions were serially diluted and then transferred to a 96-well microplate. 40 μL aliquots of each dilution were dispensed into the wells of a microplate containing 200 μL/well of artificial diet. The samples were dried at room temperature and 5–10 synchronized beet armyworm eggs suspended in 25 μL of a 1% agar solution were added to each well. The egg agar was allowed to dry and the plates covered with perforated Mylar®. After seven days, the number of live insects in each sample well was tabulated. The results are shown in Table 1

TABLE 1

AQ153 Has No Synergistic Effect with Javelin

| | Javelin ® concentration (μg) | | | | | | | | |
|---|---|---|---|---|---|---|---|---|---|
| | 41.6 | 27.4 | 18.1 | 12 | 7.9 | 5.2 | 3.4 | 2.3 | 1.5 |
| Javelin alone (#1) | 1s[a] | 1s | 3s | 5s | 11 | 14 | 13 | 22 | nd |
| Javelin alone (#2) | 1s | 2s | 3s | 6s | 17 | 22 | 19 | 17 | nd |
| Jav + AQ175 | nd | 0 | 0 | 0 | 0 | 0 | 2s | 5s | 14 |
| Jav + AQ177 | nd | 0 | 0 | 0 | 0 | 0 | 4s | 9s | 18 |
| Jav + AQ153 | nd | 1 | 7 | 11 | 12 | 19 | 18 | 18 | 15 |

[a]The "s" indicates that the living insects were extremely stunted compared to controls.

As previously shown, zwittermicin producing strains AQ175 and AQ177 enhance Javelin® inhibition of insect growth. However, AQ153 supernatant mixed with Javelin® does not produce a synergistic effect, indicating that the antibiotic produced by AQ153 is not zwittermicin-A.

Molecular Weight of the AQ153 Antibiotic

AQ153 was grown in culture and an aqueous extract was prepared as described above. A 500 μL sample of aqueous broth was applied to the top of a 10,000 dalton molecular weight (MW) Amicon microconcentrator and centrifuged at 12,000 rpm for 35 minutes. The material passing through the filter (less than 10,000 daltons MW) and the material on the filter (greater than 10,000 daltons MW) were collected and assayed in a 96-well microtiter plate as described above using both *B. cinerea* and Phytophthora. Only the material collected from the top of the filter inhibited growth of Botrytis and Phytophthora. Thus, AQ153 produces an antibiotic having a molecular weight greater than 10,000 daltons.

Heat Stability, Acid and Base Stability of the AQ153 Antibiotic

An aqueous extract of an AQ153 culture was prepared as described above. For heat stability testing, a 500 μL sample was heated to 70° C. for one hour in a water bath and tested for activity in the microtiter plate assay described above. Acid stability was tested by adding 12.5 μL of a 0.5M HCl solution to a 500 μL sample of the aqueous extract. The pH of the solution was 12 and the solution was incubated for two hours at room temperature. The solution was adjusted to pH 6.0 prior to the bioassay. Similarly, base stability was tested by adding 28 μL of a 2.5M NaOH solution to 500 μL of the aqueous extract and treating as above.

Results of the bioassay showed that the antibiotic produced by AQ153 when treated with acid or base did not inhibit fungal growth. However, both untreated and heat treated aqueous extract effectively inhibited fungal growth.

Trypsin Activity of AQ153 Aqueous Extract To determine whether a protease would inactivate the Botrytis activity of the AQ153 antibiotic, a 500 µL sample of the aqueous extract was treated with 1.2 mg of trypsin and shaken at room temperature for one hour. A control sample of the trypsin was also prepared by adding 1.2 mg of trypsin to 500 µL of water and incubating in the same manner. Samples were tested in the 96-well microplate format using 20 µL of sample per well, three wells per treatment. The Botrytis spore suspension was determined to be $7.6 \times 10^5$ spores/mL and 20 µL of this suspension was added to each well. After incubation at room temperature for five days, the plate was scored as follows: "+" indicates fungal growth, sample inactive; "++" indicates fungal growth and sporulation, sample inactive, "—" indicates no growth, sample active. Each of the three wells was scored independently. The results are shown below.

| SAMPLE | RESULT |
| --- | --- |
| AQ153 with trypsin | −, −, − |
| Trypsin control | +, +, + |

Example 2

Antibiotic activity in culture

To determine if the AQ153 antibiotic was effective against the fungi *Phytophthora infestans*, *Pythium ultimum*, *Botrytis cinerea*, *Rhizoctonia solani*, and *Alternaria solani*, the following experiments were performed. Petri plates were filled with an agar medium (PDA-potato dextrose agar, Difco). Cultures of the above fungi were grown for three days in liquid YPG-1 medium (0.4% yeast extract, 0.1% $KH_2PO$, 0.05% $MgSO_4 \cdot 7H_2O$, 1.5% glucose). 0.1–0.2 mL aliquots of spore suspension (concentration approximately $2 \times 10^6$ spores/mL) of pathogen were spread onto the agar. AQ153 was grown in potato dextrose broth (PDB) (Difco) for three days. To test whole broth cultures, the strain was grown to approximately $1 \times 10^6$ to $6 \times 10^6$ CFU/mL and aliquots were taken from these cultures. Supernatant was obtained by density centrifugation of the culture at 5,200 rpm for 20 minutes.

Two 7 mm holes were made in each petri dish. A volume of 100 µL of test sample (either supernatant or whole broth) was added to each 7 mm hole. Each test was performed in duplicate. No microorganism test sample was added to a control plate. The zone of inhibition, measured in millimeters around each hole was measured after 3 to 10 days. Results for Phytophthora, Botrytis, Rhizoctonia, Alternaria and Pythium are shown in Table 2. Control plates showed no zone of inhibition.

TABLE 2

|  | Phytophthora | Pythium | Botrytis | Rhizoctonia | Alternaria |
| --- | --- | --- | --- | --- | --- |
| Supernatant | 15 mm | 17 mm | 16 mm | 26 mm | 25 mm |
| Whole broth | 13 mm | 18 mm | 16 mm | Not done | 26 mm |

The same experiment above was performed using a different medium (dextrose, bactopeptone, yeast extract, malt extract) and including the gram-negative bacterium *Pseudomonas syringae*, an important plant pathogen. The results are shown in Table 3.

TABLE 3

|  | Phytophthora | Pythium | Botrytis | Rhizoctonia | Alternaria | Pseudomonas |
| --- | --- | --- | --- | --- | --- | --- |
| Supernatant | Not done | No zone | Not done | No zone | No zone | 8 mm |

The same experiment was repeated to test AQ153 against the fungus *Trichoderma harzianum*, an important pathogen of mushrooms. *Trichoderma harzianum*, strain T-14, was obtained from Campbell. (Davis, Calif.). A number four cork borer was used to make four wells in PDA plates. AQ153 was applied to one of the four wells. Two discs of number four cork borer-sized Trichoderma mycelial plugs were added to each plate in between two wells on each side of the plate. Results were recorded 24 hours later. The size of the cleared zone between the bacterium and the mycelium was recorded. AQ153 produced a 4 mm zone.

To determine in vitro effectiveness of AQ153 against the gram-negative bacterium, *Erwinia herbicola*, and the fungus, *Monilinia fructicola*, the following experiment was conducted. Bacterial strains were cultured as described above. *Monilinia fructicola* cultures were grown on V-8 agar (20 g agar, 4 g $CaCO_3$, 200 mL V-8 juice) in the dark at room temperature for 8 days. Spores were harvested by placing sterile distilled water on the surface of the culture plates and scraping the surface with a sterile needle to dislodge the spores. Spore concentration was adjusted to $3.3 \times 10^6$ spores/mL and 400 µl added to 4 mL of soft potato dextrose agar. This mixture was poured over the surface of potato dextrose agar culture places and the soft agar allowed to solidify. *Erwinia herbicola* was fermented overnight in half-strength TSA and $1 \times 10^5$ cells were spread on a TSA agar plate. Using a sterile no. 4 cork borer, 5 wells were made in each plate and 100 µl of a three day old culture of AQ153 was added to each well. Plates were incubated at room temperature in the dark and the zones of no growth of the around each well measured. Results are summarized in Table 4.

TABLE 4

| Bacterial inhibition of *M. fructicola* and *E. herbicola* | | |
| --- | --- | --- |
|  | *M. fructicola* | *E. herbicola* |
| AQ153 | 22 mm | Rep1 = 23 mm |
|  |  | Rep 2 = 27 mm |

Example 3

Antibiotic activity using whole plants

The ability of the AQ153 antibiotic to control late blight (*P. infestans*) infection was tested on whole tomato plants.

Tomato plants (Ace and Patio varieties) were purchased from Ace hardware and transplanted into 6 packs having three plants per pack. AQ153 was grown in Trypticase Soy Broth (TSB) (Difco) for 72 hours and reached a concentration of $5 \times 10^6$ CFU/mL. One plant of each variety of tomato plant was sprayed to runoff with a whole broth culture or supernatant of AQ153 and then air-dried at approximately 21° C. Two control plants were untreated. All plants were then sprayed to runoff with a *P. infestans* culture at $1.55 \times 10^5$ CFU/mL. The plants were air-dried at 21° C., lightly misted with deionized water, enclosed in a clear plastic bag and incubated at approximately 16° C. The amount of late blight infestation was recorded fifteen days after treatment. Results are shown in Table 5.

TABLE 5

Light blight and bacterial speck infection fifteen days after treatment with AQ153

| Bacterial strain - Tomato Plant Ace(A) Patio (P) | Whole Broth or Supernatant | # infected leaves/# of total leaves | Percent Infection | Bacterial Speck Infection |
|---|---|---|---|---|
| AQ153(A) | supernatant | 4/34 | 11.7 | No |
| AQ153(P) | supernatant | 3/32 | 9.4 | bacterial |
| Average |  |  | 10.6 | speck |
| AQ153(A) | whole broth | 7/37 | 18.9 |  |
| AQ153(P) | whole broth | 3/25 | 12.0 |  |
| Average |  |  | 15.5 |  |
| Phytophthora |  |  |  |  |
| untreated control |  |  |  | 100% covered with speck |
| (A) |  | 6\26 | 23.1 | Full of bacterial speck |
| (P) |  | 4\32 | 12.5 | Full of bacterial speck |
| Average |  |  | 17.8 |  |

These results show that the antibiotic-producing strain within the present invention is effective against late blight and bacterial speck.

Example 4

Antibiotic activity of AQ153 against *B. cinerea*

To test the effectiveness of the antibiotic-producing bacterial strain AQ153 of the present invention against *B. cinerea*, fresh strawberries picked the day of testing were utilized. For test #1, frozen supenatant of AQ153 was used. AQ153 was grown in potato dextrose broth as previously described. The supernatants were frozen for 1 to 1.5 months before testing. In test #2, AQ153 was grown in either half-strength TSB or in potato dextrose broth (PDB) and the broth or supernatant tested without freezing. Whole broth cultures and supernatants were sprayed onto the strawberries until runoff, then allowed to air dry.

*B. cinerea* spores were grown on potato dextrose agar in a petri plate and scraped into de-ionized water to form a liquid inoculum. The *B. cinerea* inoculum, measuring approximately $5.8 \times 10^5$ cells per mL was sprayed onto the berries until runoff, and the berries allowed to air dry. In test #1, the berries were placed inside a cardboard container with plastic wrap lid at 25° C. In test #2, all berries were place uncovered in an incubator at approximately 16° C. Results are shown in Table 6.

TABLE 6

| Botrytis test Bacterial strain | No. Strawberries per treatment | # infected/# clean |
|---|---|---|
| Test #1 |  |  |
| 153 frozen supernatant | 3 | 0/3 |
| Untreated Control | 3 | 3/0 |
| Test #2 |  |  |
| 153(PDB) whole broth | 2 | 0/2 |
| 153(PDB) supernatant | 2 | 0/2 |
| 153(TSB) whole broth | 2 | 0/2 |

TABLE 6-continued

| Botrytis test Bacterial strain | No. Strawberries per treatment | # infected/# clean |
|---|---|---|
| 153(TSB) supernatant | 2 | 1/2 |
| Untreated control | 2 | 1/1 |

AQ153 frozen supernatant was completely effective at inhibiting *B. cinerea* infection on live strawberry plants. In addition, the whole broth culture of AQ153 was completely effective at preventing *B. cinerea* infection, regardless of the medium used. Supernatant from AQ153 grown in TSB was partially effective but, when grown in PDB, was 100% effective against *B. cinerea*.

Example 5

Antibiotic Activity of AQ153 Against Fungal Pathogens

To test the antibiotic-producing bacterial strain AQ153 against a number of fungal pathogens, AQ153 was grown in potato dextrose broth. Cells were cultured to $5 \times 10^6$ cells/mL. Replicates of three test plants and three control plants per pathogen were utilized. The test plants were each sprayed with a whole broth culture of AQ153 to run-off with a hand-held sprayer. When the foliage had dried, each test plant was sprayed a second time. After the second application of the bacterial strain culture has dried, the test plants and the control plants were inoculated with the appropriate fungal pathogen. Plants were incubated under conditions conducive to disease development. In addition, positive controls were utilized by testing known pesticides against appropriate fungal pathogens in the same manner as the culture of the bacterial strain was tested. Each plant was evaluated by estimating the percent disease control using a scale from 0% control to 100% control. (0=disease level of untreated control; 100=plants with no visible lesions). The fungal pathogens, resulting diseases, host plant and control pesticides are presented in Table 7. The results are shown in Table 8.

TABLE 7

| Disease | Pathogen | Host Plant | Standard Pesticide |
|---|---|---|---|
| Late Blight | Phytophthora infestans | tomato | metalaxyl |
| Early Blight | Alternaria solani | tomato | propiconazole |
| Gray Mold | Botrytis cinerea | pepper | propiconazole |
| Downy Mildew | Plasmopara viticola | grape | metalaxyl |
| Powdery Mildew | Uncinula necator | grape | propiconazole |
| Leaf Rust | Puccinia recondita f.sp tritici | wheat | propiconazole |
| Glume Blotch | Staganospora nodorum | wheat | propiconazole |

TABLE 8

| Treatment | Rate (ppm) | % disease control ||||||| 
| | | Pi$^y$ | As | Pv | Un | Bc | Sn | Pr |
|---|---|---|---|---|---|---|---|---|
| AQ153 | — | 7 | 0 | 100 | 0 | 100 | 0 | 73 |
| metalaxyl | 30 | 90 | — | 100 | — | — | — | — |
|  | 20 | — | — | 67 | — | — | — | — |
|  | 10 | 47 | — | — | — | — | — | — |
| myclobutanil | 10 | — | — | — | 100 | — | — | — |
|  | 1 | — | — | — | 0 | — | — | — |
| propiconazole | 250 | — | 93 | — | — | — | — | — |
|  | 30 | — | 37 | — | — | — | — | — |
|  | 10 | — | — | — | — | 100 | 100 | — |
|  | 5 | — | — | — | — | 63 | 73 | 95 |
|  | 1 | — | — | — | — | — | — | 33 |
| Disease Index (%)$^z$ | — | 50 | 80 | 75 | 30 | 80 | 80 | 80 |

$^y$Pi = P. infestans, As = A. solani, Pv = P. viticola, Un = U. necator, Bc = B. cinerea, Sn = S. nodorum, Pr = P. recondita f.sp. tritici.
(%)$^z$Disease index = percent diseased tissue on the untreated, inoculated plants.

AQ153 provided complete control of *B. cinerea*. AQ153 was also highly active against grape downy mildew and leaf rust, and had slight activity against Phytophthora in this test.

Example 6

Activity of AQ153 against brown rot, *Monilinia fructicola*

A 250 mL culture of AQ153 was grown for 3.5 days in PDB as previously described. Peaches were purchased from a local grocery store (Safeway) and were surface sterilized with a 10% Clorox solution, rinsed with deionized water and air dried. Whole fermentation broths of AQ153 (8.7×10$^6$ CFU/mL) were sprayed with a hand-held sprayer on two peaches until runoff (approximately 50 mL per two peaches). The peaches were allowed to air dry. Monilinia spores were scraped from a petri plate and suspended in deionized water to a concentration of 1.09×10$^5$ spores/mL. The peaches were then sprayed with the spore suspension until runoff and allowed to air dry. Two peaches were untreated and two peaches were sprayed with Monilinia only. The peaches were placed in a polypropylene container in an incubator in the dark at 18° C. for four or six days. The amount of brown rot on each peach was measured, as show in Table 9.

TABLE 9

| AQ153 Inhibition of Monilinia in Peaches | | |
|---|---|---|
|  | Size of Monilinia Lesion after 4 days | Size of Monilinia Lesion after 6 days |
| AQ153 treated #1 | 1.5 × 1 cm | 5 × 5 cm |
| AQ153 treated #2 | No infection | No infection |
| Untreated #1 | 9 × 7 cm | 11 × 7 cm |
| Untreated #2 | 3 × 2 cm | 11 × 12 cm |
| Monilinia treated #1 | 7 × 5 cm | 10 × 10 cm |
| Monilinia treated #2 | 4 × 3 cm | 10 × 6 cm |

At both four and six days, AQ153 suppressed Monilinia brown rot compared to the untreated controls and Monilinia only peaches. After six days, the control peaches were all heavily infected with brown rot, while only one of the AQ153 peaches showed infection. Furthermore, the one infected AQ153 peach had a lesion which was much smaller than those in the untreated or Monilinia only controls.

Comparison of AQ153 and Chemical Fungicide Inhibition of *Monilinia fructicola*

Using the same protocol as described above to grown AQ153 cultures and Monilinia spores, the effect of AQ153 was compared to the commercially available fungicide Benlate® (benomyl). Results are shown in Table 10.

TABLE 10

| AQ153 and Benlate ® Inhibition of Monilinia in Peaches | | |
|---|---|---|
|  | Size of Monilinia Lesion after 4 days | Size of Monilinia Lesion after 6 days |
| AQ153 treated #1 | 1.5 × 1.0 cm | 3 × 4 cm |
| AQ153 treated #2 | No infection | No infection |
| Benlate ® treated #1 | 1.25 cm × 1.0 cm | 3 × 3 cm |
| Benlate ® treated #2 | No infection | No infection |
| Monilinia treated #1 | 3.5 × 3.5 cm | 5 × 7 cm |
| Monilinia treated #2 | No infection | No infection |

These results show that AQ153 is as effective in controlling Monilinia infection as the commercial fungicide, Benlate®.

Having now fully described this invention, it will be appreciated by those skilled in the art that the same can be performed within a wide range of equivalent parameters, concentrations and conditions without departing from the spirit and scope of the invention and without undue experimentation. While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows the scope of the appended claims.

What is claimed is:

1. A method for protecting or treating plants from fungal and bacterial infections comprising applying to the plant an effective amount of an antibiotic-producing *Bacillus subtilis* strain AQ153 (ATCC 55614) or a soluble extract or culture supernatant obtained therefrom.

2. The method of claim 1 wherein the infection is caused by a microorganism selected from the group consisting of *Phytophthora infestans*, *Botrytis cinerea*, *Pseudomonas syringae*, *Erwinia herbicola*, *Alternaria solani*, *Trichoderma harzianom*, *Monilinia fructicola*, *Puccinia recondita*, *Rhizoctonia solani*, *Pythium ultimum*, and *Plasmopara viticola*.

3. The method of claim 1 wherein the antibiotic-producing *Bacillus subtilis* strain is applied to the plant as a whole broth culture.

4. The method of claim 3 wherein the culture is diluted.

5. The method of claim 1 wherein the culture supernatant is applied to the plant.

6. The method of claim 5 wherein the supernatant is refrigerated or frozen prior to application to the plant.

7. The method of claim 5 wherein the supernatant is diluted.

8. The method of claim 1 wherein said antibiotic-producing bacterial strain is applied as a wettable powder, granules, aqueous flowable, dry flowable or is microencapsulated in a suitable substance.

9. The method according to claim 1 wherein the antibiotic-producing bacterial strain is applied in combination with a chemical pesticide.

* * * * *